(12) United States Patent
Jeevanandam

(10) Patent No.: US 11,338,123 B2
(45) Date of Patent: May 24, 2022

(54) BLOOD PUMP DEVICES AND ASSOCIATED SYSTEMS AND METHODS

(71) Applicant: NuPulseCV, Inc., Raleigh, NC (US)

(72) Inventor: Valluvan Jeevanandam, Chicago, IL (US)

(73) Assignee: NuPulseCV, Inc., Raleigh, NC (US)

( * ) Notice: Subject to any disclaimer, the term of this patent is extended or adjusted under 35 U.S.C. 154(b) by 388 days.

(21) Appl. No.: 16/265,769

(22) Filed: Feb. 1, 2019

(65) Prior Publication Data

US 2019/0231951 A1 Aug. 1, 2019

Related U.S. Application Data

(60) Provisional application No. 62/625,181, filed on Feb. 1, 2018.

(51) Int. Cl.
| | | |
|---|---|---|
| *A61M 39/02* | (2006.01) | |
| *A61M 60/274* | (2021.01) | |
| *A61M 60/40* | (2021.01) | |
| *A61M 60/50* | (2021.01) | |
| *A61M 60/135* | (2021.01) | |
| *A61M 60/268* | (2021.01) | |
| *A61M 60/892* | (2021.01) | |
| *A61M 60/148* | (2021.01) | |
| *A61M 60/857* | (2021.01) | |

(52) U.S. Cl.
CPC .......... *A61M 60/274* (2021.01); *A61M 39/02* (2013.01); *A61M 60/135* (2021.01); *A61M 60/268* (2021.01); *A61M 60/40* (2021.01); *A61M 60/50* (2021.01); *A61M 60/892* (2021.01); *A61M 60/148* (2021.01); *A61M 60/857* (2021.01); *A61M 2205/0216* (2013.01); *A61M 2205/0266* (2013.01); *A61M 2205/3523* (2013.01); *A61M 2230/06* (2013.01)

(58) Field of Classification Search
CPC combination set(s) only.
See application file for complete search history.

(56) References Cited

U.S. PATENT DOCUMENTS

| | | | |
|---|---|---|---|
| 3,606,592 A | | 9/1971 | Madurski |
| 4,034,742 A | * | 7/1977 | Thoma ............... A61M 60/892 600/17 |
| 5,332,403 A | | 7/1994 | Kolff |

(Continued)

FOREIGN PATENT DOCUMENTS

| | | |
|---|---|---|
| EP | 1466635 | 10/2004 |
| EP | 1466635 A1 | 10/2004 |

(Continued)

OTHER PUBLICATIONS

International Search Report, PCT/US2019/016410, dated May 14, 2019, 15 pages.

*Primary Examiner* — Scott Luan
(74) *Attorney, Agent, or Firm* — Loeb & Loeb LLP

(57) ABSTRACT

The present technology provides a blood pump device and associated systems and methods of use thereof to assist blood circulation in a patient. The blood pump device includes a flexible member disposed within a housing. Movement of the flexible member in the housing varies the volume of chambers within the housing and effectuates pumping of blood to and from a vessel in fluid connection with a chamber of the blood pump device.

16 Claims, 8 Drawing Sheets

(56) References Cited

U.S. PATENT DOCUMENTS

| | | |
|---|---|---|
| 7,066,874 B2 * | 6/2006 | Riebman ............. A61M 60/274 600/16 |
| 7,128,749 B1 | 10/2006 | Vargas et al. |
| 7,892,162 B1 | 2/2011 | Jeevanandam |
| 8,066,628 B1 | 11/2011 | Jeevanandam |
| 8,323,174 B2 | 12/2012 | Jeevanandam |
| 8,326,421 B2 | 12/2012 | Jeevanandam |
| 8,608,637 B2 | 12/2013 | Jeevanandam |
| 8,684,905 B2 | 4/2014 | Jeevanandam |
| 9,265,871 B2 | 2/2016 | Jeevanandam |
| 9,566,374 B2 | 2/2017 | Spence et al. |
| 9,592,328 B2 | 3/2017 | Jeevanandam |
| 9,950,102 B2 | 4/2018 | Spence et al. |
| 10,137,230 B2 | 11/2018 | Novack |
| 10,518,009 B2 | 12/2019 | Jeevanandam |
| 2005/0096496 A1 | 5/2005 | Spence |
| 2006/0052659 A1 | 3/2006 | Topaz |
| 2017/0290966 A1 * | 10/2017 | Botterbusch ........ A61M 60/268 |
| 2018/0055981 A1 | 3/2018 | Smith |
| 2018/0099078 A1 * | 4/2018 | Tuseth ................ A61M 60/135 |
| 2019/0184077 A1 | 6/2019 | Novack |
| 2019/0231951 A1 | 8/2019 | Jeevanandam |
| 2020/0086021 A1 | 3/2020 | Jeevanandam |

FOREIGN PATENT DOCUMENTS

| | | |
|---|---|---|
| WO | 2012/004618 A1 | 1/2012 |
| WO | 2012004618 | 1/2012 |

* cited by examiner

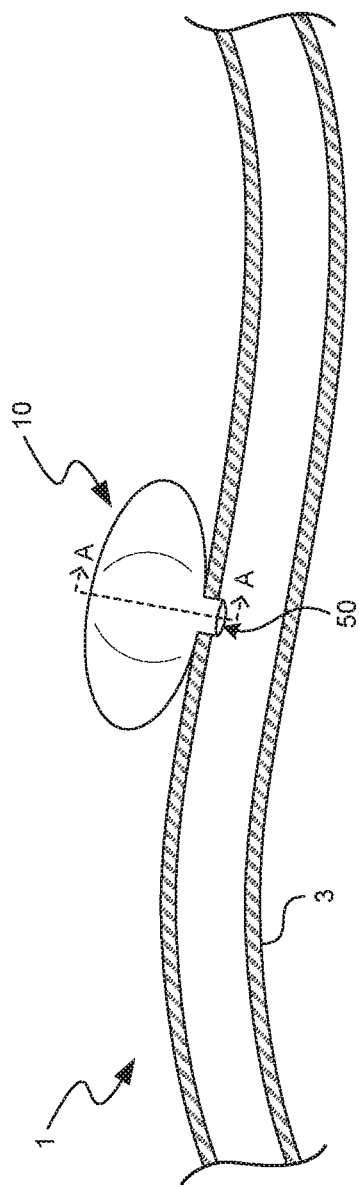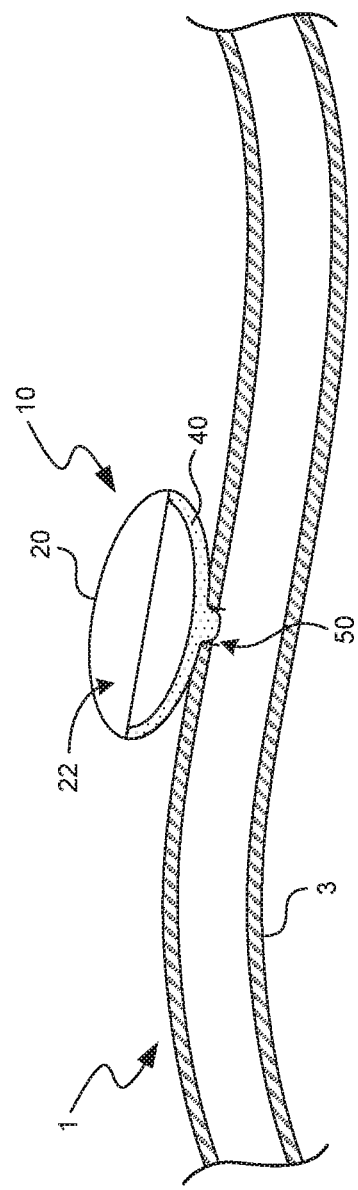

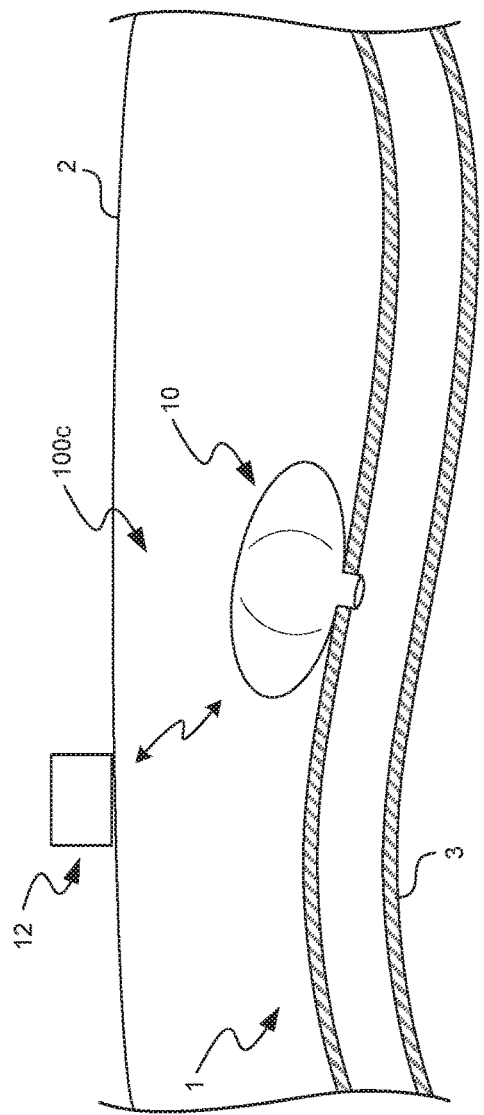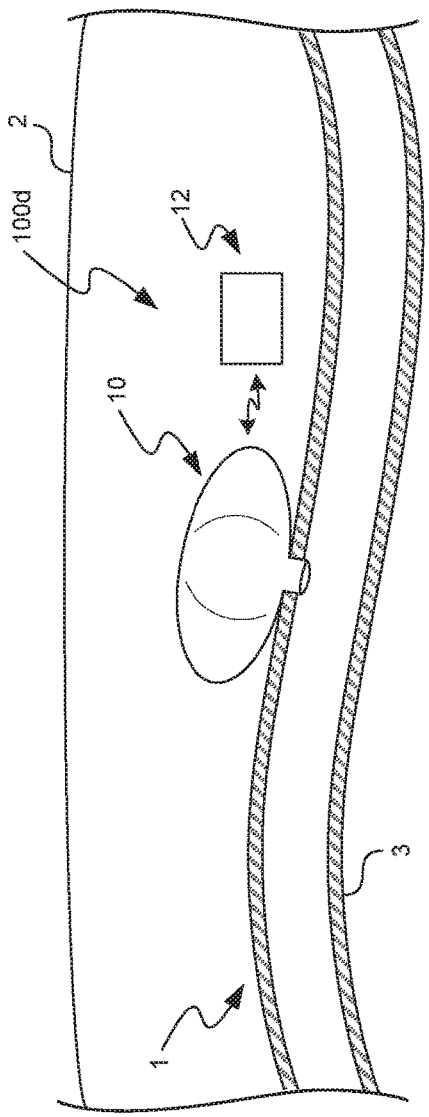

BLOOD PUMP DEVICES AND ASSOCIATED SYSTEMS AND METHODS

CROSS-REFERENCE TO RELATED APPLICATION(S)

This application claims the benefit of U.S. Provisional Patent Application No. 62/625,181, filed Feb. 1, 2018, the disclosure of which is hereby incorporated by reference in its entirety.

TECHNICAL FIELD

The present technology relates generally to medical devices, and more particularly to blood pump devices for cardiac insufficiency and associated methods and systems.

BACKGROUND

Mechanical heart support systems continuously become more and more prevalent as a therapeutic method for treating chronic cardiac insufficiency. Their main task consists of maintaining blood circulation, thus ensuring an adequate supply of oxygen to organs and tissues in cases of heart failure. More recent developments in the realm of mechanical circulatory support systems have led to the creation of pump mechanisms which, depending on the clinical indication, range from unilateral ventricular assist devices (VAD) to total heart replacement or artificial heart (TAH) systems. Presently, the clinical demand for ventricular assist devices is considerably higher than the demand for total artificial heart systems, and left-ventricular assist devices (LVAD) are of special significance due to the higher hemodynamic load on the left half of the heart.

A major therapeutic objective of an assist device is to provide a "bridge-to-transplant", wherein the VAD system takes over or assists the pumping capacity of the insufficient heart until a suitable donor organ becomes available and a heart transplantation can be performed. VADs are implantable blood pumps used for both short-term and long-term applications where a patient's heart is incapable of providing adequate circulation. A patient suffering from heart failure may use a VAD while awaiting a heart transplant. In another example, a patient may use a VAD while recovering from heart surgery. Thus, a VAD can supplement a weak heart or can effectively replace the natural heart's function. VADs can be implanted in the patient's body and powered by an electrical power source outside the patient's body.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIG. 1 is an illustration of a blood pump device implanted adjacent to a blood vessel in accordance with embodiments of the present technology.

FIG. 2 is a longitudinal cross-sectional view of the blood pump device of FIG. 1 configured in accordance with embodiments of the present technology.

FIG. 3C is a partially schematic illustration of a blood pumping system having an actuator mechanism in accordance with embodiments of the present technology.

FIG. 3D is a partially schematic illustration of a blood pumping system having an implantable actuator mechanism in accordance with embodiments of the present technology.

DETAILED DESCRIPTION

Figure 3A:
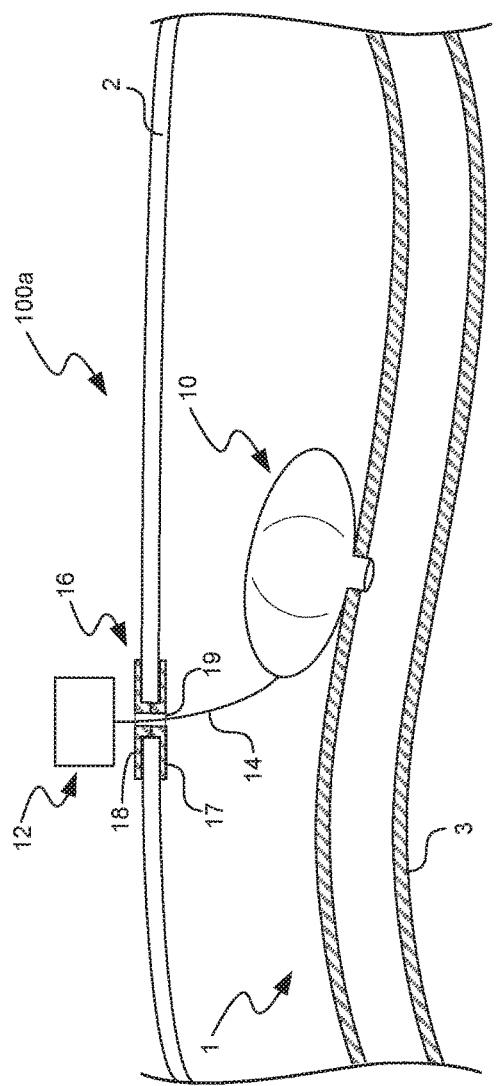
FIG. 3A is a partially schematic illustration of a blood pumping system having an external actuator mechanism in accordance with embodiments of the present technology.
Figure 3B:
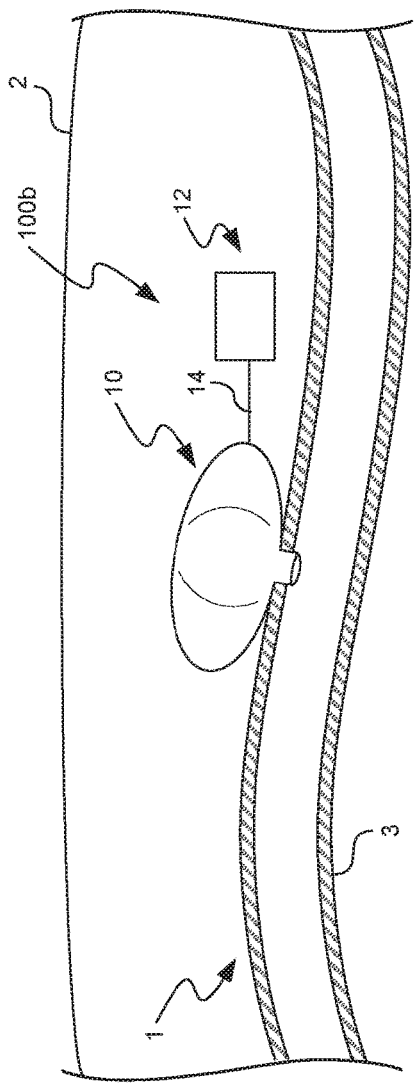
FIG. 3B is a partially schematic illustration of a blood pumping system having an implantable actuator mechanism in accordance with embodiments of the present technology.

This present technology is generally directed to blood pump devices for cardiac insufficiency and associated systems and methods. For example, embodiments disclosed herein provide an on-demand blood pump that exhibits exemplary blood flow characteristics. Specific details of several embodiments of the present technology are described herein with reference to drawings. Although many of the embodiments are described with respect to devices, systems, and methods for regulating blood flow through arterial vessels, such as the subclavian artery, other embodiments in addition to those described herein are within the scope of the present technology. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

The terms "pump", "blood pump", "device", "pump device", and "blood pump device" are used interchangeably herein to refer to certain embodiments of the present technology. Moreover, relative terms such as, for example, "substantially", "approximately", and "about" are used herein to mean the stated value plus or minus 10%.

Some embodiments of the blood pump device disclosed herein can include a housing that defines an internal reservoir having a fixed volume. A flexible member, such as a diaphragm, can be disposed within the internal reservoir and divide the reservoir into a first chamber and a second chamber. The first chamber can include a fluid outlet fluidly coupled to a blood vessel upon implantation to allow for fluid passage between the first chamber and the blood vessel.

In some embodiments, the device is configured to transition between a first state or configuration and a second state or configuration (e.g., via movement of the flexible member). When the blood pump is in the first configuration, the second chamber has a first volume substantially equal to the internal reservoir fixed volume and the first chamber can have a volume that is substantially null. When the blood pump is in the second configuration, the second chamber can have a second volume less than the internal reservoir fixed volume and the volume of the first chamber can increase due to the movement of the flexible member within the internal reservoir. The transition from the first configuration to the second configuration by movement of the flexible member can generate negative pressure in the first chamber, thereby drawing fluid from the blood vessel into the first chamber through the outlet. The transition from the second configuration to the first configuration can generate positive pressure in the first chamber, thereby pushing fluid out of the first chamber into the blood vessel through the outlet. Based on this movement, the blood pump device can be configured to work in a pulsatile fashion synchronized with a patient's heartbeat for any given number of beats. Movement of the flexible member between the first and second configurations can be controlled by an actuator mechanism that is transitionable between a first state (e.g., a passive or non-activated state) and a second state (e.g., an active state). When the actuator is in the first state, the blood pump can be in the first configuration with no or substantially no fluid (e.g., blood) within the first chamber. When the actuator mechanism is in the second state, the blood pump can be in the second configuration thereby drawing fluid into the first chamber. Therefore, the blood pump device can remain in a first state with no or substantially no fluid in the internal reservoir for an indefinite amount of time. The blood pump can then be activated and cycled between the first and second configuration for any given amount of time in synchrony with a patient's heartbeat. The blood pump can be returned to the first state after operation, with no or substantially no fluid in the first chamber. The ability to remain in the first state for any amount of time while retaining no or substantially no fluid (e.g., blood) in the internal volume of the pump reduces or eliminates the risk of blood stagnation and the potential of blood clots forming in the internal reservoir.

The present technology further provides a method for assisting blood circulation in a patient utilizing the blood pump devices disclosed herein. The method can include coupling the outlet of the blood pump device to a blood vessel of a patient; drawing blood from the blood vessel into the first chamber by actuating the actuator mechanism; and expelling blood from the first chamber though the outlet into the blood vessel. In some embodiments, expulsion of blood from the first chamber is accomplished by deactivating the actuator mechanism. The activation of the blood pump device can be timed in accordance with the patient's heartbeat such that blood is drawn into the first chamber during systole and expelled from the first chamber during diastole.

Selected Embodiments of Blood Pump Systems

FIGS. 1-3D illustrate various aspects of blood pump systems configured in accordance with the present technology. FIGS. 1 and 2 are side and cross-sectional views of a blood pump device 10 positioned adjacent to a blood vessel 1. As illustrated in FIG. 1, the blood pump device 10 can include a fluid connection or outlet portion 50 that extends into or through the vessel wall such that an opening 51 of the outlet portion 50 is placed in fluid communication with the blood vessel 1. The blood pump device 10 can facilitate the movement of blood through the blood vessel 1 by alternating between pulling blood into the blood pump device 10 through the outlet portion 50 and pushing blood out of the blood pump device 10 back into the blood vessel 1 through the outlet portion 50. For example, as shown in FIG. 2, the blood pump device 10 can include a housing 20 defining an internal chamber 22 and a flexible member 40 (also referred to as a "flexible membrane 40") positioned within the housing 20. The flexible member 40 can move within the internal chamber 22 during diastole and systole to drive blood into and out of the internal chamber 22 via the outlet portion 50. Specific features of the blood pump device 10 are described in greater detail below with respect to FIGS. 4-8.

FIGS. 3A-3D illustrate blood pumping systems (identified individually as blood pumping systems 100a-100d, respectively; referred to collectively as "blood pumping systems 100" or "systems 100") including the blood pump device 10 of FIGS. 1 and 2 configured in accordance with embodiments of the present technology. The blood pumping systems 100 include an actuator mechanism 12 configured to facilitate the transition of the blood pump device 10 back and forth between a first and second configuration (e.g., via movement of the flexible member 40 of FIG. 2). In the embodiments illustrated in FIGS. 3A and 3C, the actuator mechanism 12 is positioned external to a skin barrier 2 (e.g., positioned outside a patient's body as a wearable or other device), and in the embodiments illustrated in FIGS. 3B and 3D the actuator mechanism 12 is implanted within the patient's body under the skin barrier 2. Whether positioned externally or internally, the actuator mechanism 12 can be operatively connected to the blood pump device 10 via a wire or other physical connection 14 (FIGS. 3A and 3B) or via a wireless connection (FIGS. 3C and 3D), such as via a Bluetooth, radio, WiFi, and/or other wireless connection means.

As shown in FIG. 3A, when the system 100a includes an external actuator mechanism 12 with a physical connection 14 to the blood pump device 10, the system 100a can further include a skin interface device 16 that has a first portion 17 positioned at least partially internal to the patient's body (i.e., through or under the skin 2), a second portion 18 at least partially external to the patient's body (i.e., on and/or extending into the skin 2), and a conduit or channel 19 extending through the first and second portions to provide an access site for communication between the external actuator mechanism 12 and the implanted blood pump device 10. In some embodiments, the channel 19 can house a portion of the wire 14 and/or other components extending between the implanted blood pump device 10 and the externally-positioned actuator mechanism 12. In some embodiments, the first portion 17 can be configured to connect to or receive a first wired connector coupled to the blood pump device 10, the second portion 18 can be configured to connect to or receive a second wired connector coupled to the actuator mechanism 12, and the first and second wired connectors can be communicatively coupled to each other via the skin interface device 16. In some embodiments, the first and second portions 17 and 18 and/or sections thereof can be rotatable with respect to one another to allow for movement of the internal and external system components relative to each other without tugging or aggravating the tissue adjacent the skin interface device 16. In some embodiments, the first and second portions 17 and 18 are integrally formed with each other or otherwise fixed to each other. In some embodiments, the skin interface device 16 can be similar to or the same as one or more of the skin interface devices described in U.S. Pat. No. 9,265,871, filed Sep. 3, 2014 and entitled SKIN INTERFACE DEVICE FOR CARDIAC ASSIST DEVICE, and in U.S. patent application Ser. No. 14/659,375 (Pub. No. 2015/0258261), filed Mar. 16, 2015 and entitled SKIN INTERFACE DEVICE HAVING A SKIN ATTACHMENT DEVICE AND METHOD TO IMPLANT SAME, the entire disclosures of which are each hereby incorporated by reference herein.

Figure 4:
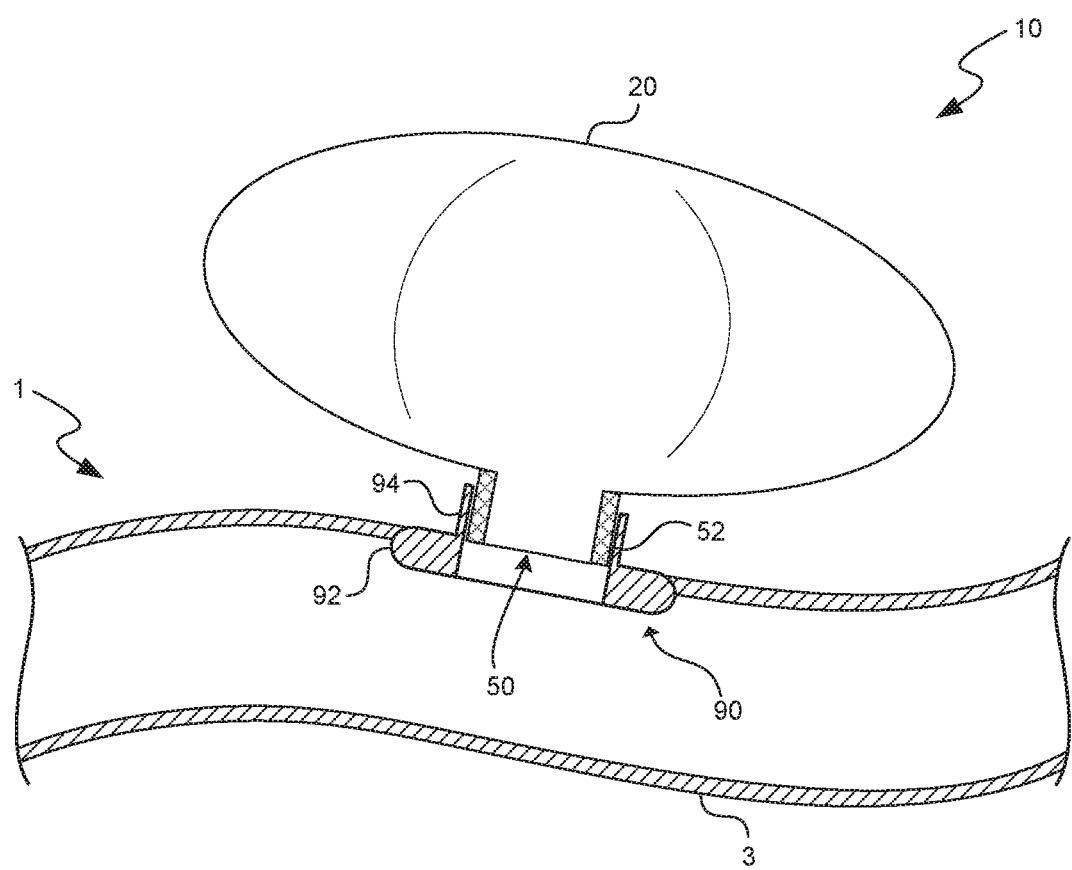
FIG. 4 is an enlarged partial cross-sectional view of a blood pump device attached to a blood vessel in accordance with embodiments of the present technology.

FIG. 4 is an enlarged partial cross-sectional view of the blood pump device 10 of FIGS. 1-3D illustrating a device-to-vessel connection in accordance with embodiments of the present technology. As illustrated in FIG. 4, the blood pump device 10 can further include a blood vessel interface structure 90 ("interface structure 90") that facilitates suturing and/or otherwise coupling the blood pump device 10 to the blood vessel wall 3. The interface structure 90 can be sized and shaped to secure blood pump device 10 the blood vessel wall 3. As shown in FIG. 4, for example, the interface structure 90 can have a ring-like shape with a flange 92 or other radially extending portion(s) configured to be positioned within the blood vessel 1 and anchor the interface structure 90 to an interior surface of the blood vessel wall 3 to avoid unintentional detachment of the blood pump device 10 from the blood vessel 1. In some embodiments, the flange 92 is configured to cooperate with an outer surface of the housing 20 of the blood pump device 10 to squeeze, wedge, sandwich, or otherwise anchor a portion of the blood vessel wall between the flange 92 and the housing 20. In some embodiments, the interface structure 90 can include a second flange (not shown) configured to be positioned against an external surface of the vessel wall 3 such that the two flanges can oppose one another to anchor the interface structure 90 and the blood pump device 10 in place. In additional or alternative embodiments, the interface structure 90 can have different shapes and/or components that facilitate vessel attachment. The interface structure 90 can further include a plurality of holes (not shown) extending through the flanged portion or other portion of the structure 10 and designed to facilitate the suturing of the interface structure 90 to the blood vessel wall 3.

The interface structure 90 can include features that mate with or otherwise attach to the outlet portion 50 of the blood pump device 10. In some embodiments, the interface structure 90 can include an extension portion 94 sized and shaped to fit around or within the outlet portion 50. As shown in FIG. 4, for example, the extension portion 94 can be a tubular structure that is shaped to receive an end section 52 of the outlet portion 50 to place the blood pump device 10 in fluid connection with the blood vessel 1. In some embodiments, the interface structure 90 can be configured to attach to an additional or other portion of the blood pump device 10. In various embodiments, the interface structure 90, the end section 52, and/or another portion of the blood pump device 10 can include threads, high friction surfaces, bayonet fittings, and/or other attachment features that facilitate secure attachment between the blood pump device 10 and the interface structure 90. In other embodiments, the interface structure 90 can be integrally formed with the blood pump device 10. For example, the interface structure 90 can be an integral extension of or fixedly attached to the outlet portion 50.

In operation, a physician can first attach the interface structure 90 to the wall of the blood vessel 1, and then couple the outlet portion 50 of the blood pump device 10 to the interface structure 90 to place the blood pump device 10 in fluid communication with the blood vessel 1. In such embodiments, the end section 52 of the outlet portion 50 can mate with the extension 94 of the interface device 90 via a friction fit or other suitable attachment means. Alternatively or additionally, the end section 52 itself can include a flange, cuff, or ring that can be sutured or otherwise connected to the blood vessel wall.

Selected Embodiments of Blood Pump Devices

Figure 5:
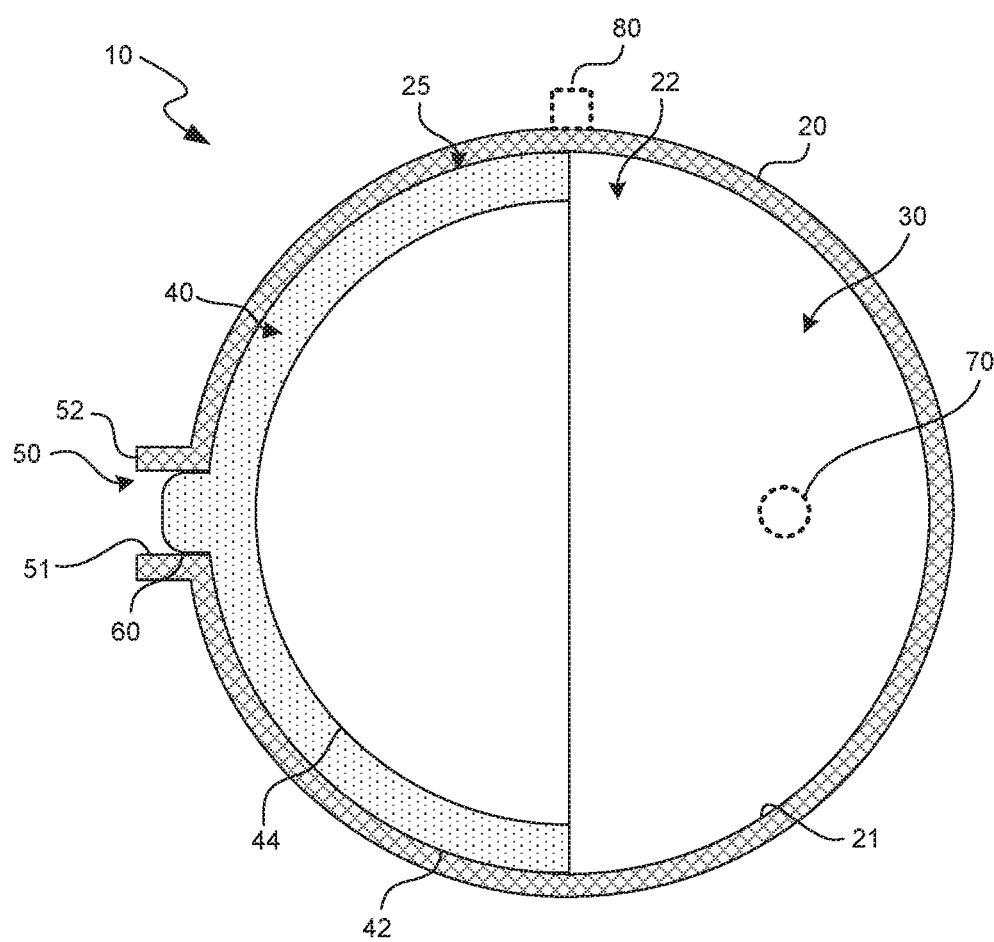
FIG. 5 is a cross-sectional view of a blood pump device in a first state in accordance with embodiments of the present technology.
Figure 6:
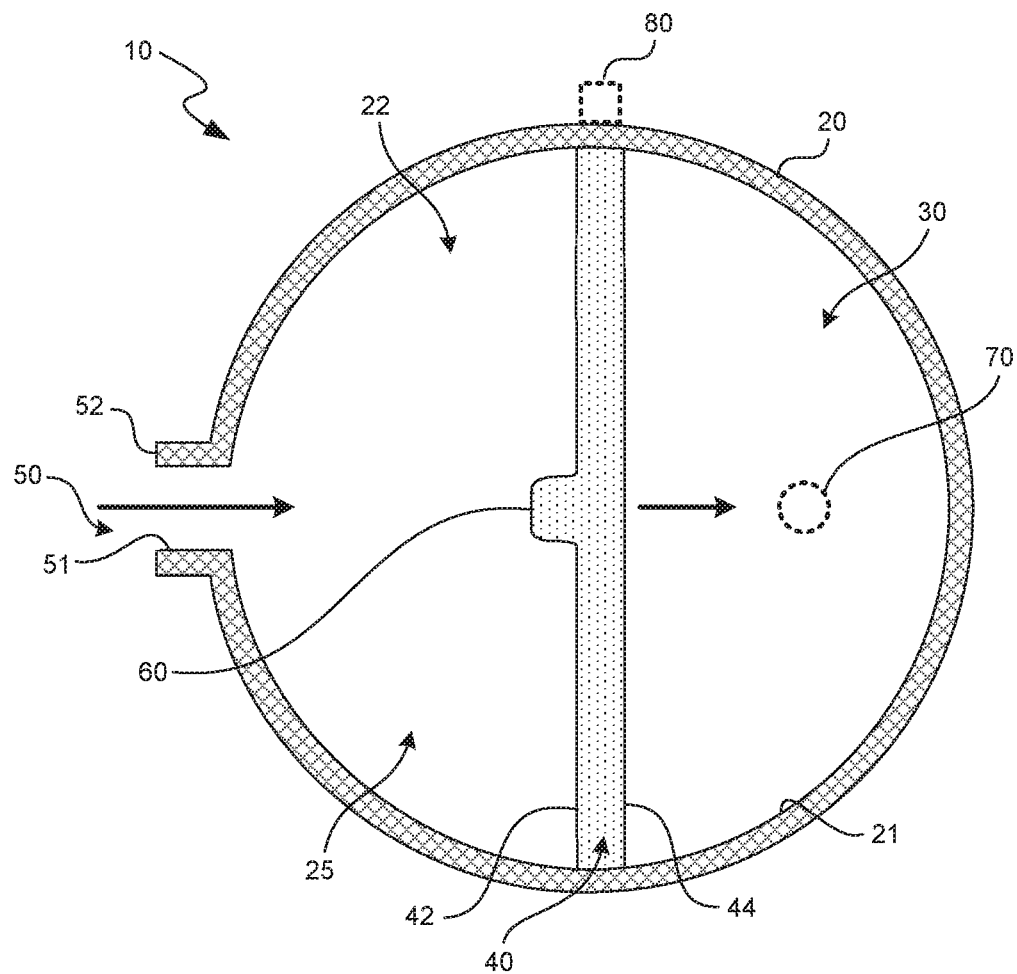
FIG. 6 is a cross-sectional view of the blood pump device of FIG. 5 transitioning between the first state and a second state in accordance with embodiments of the present technology.
Figure 7:
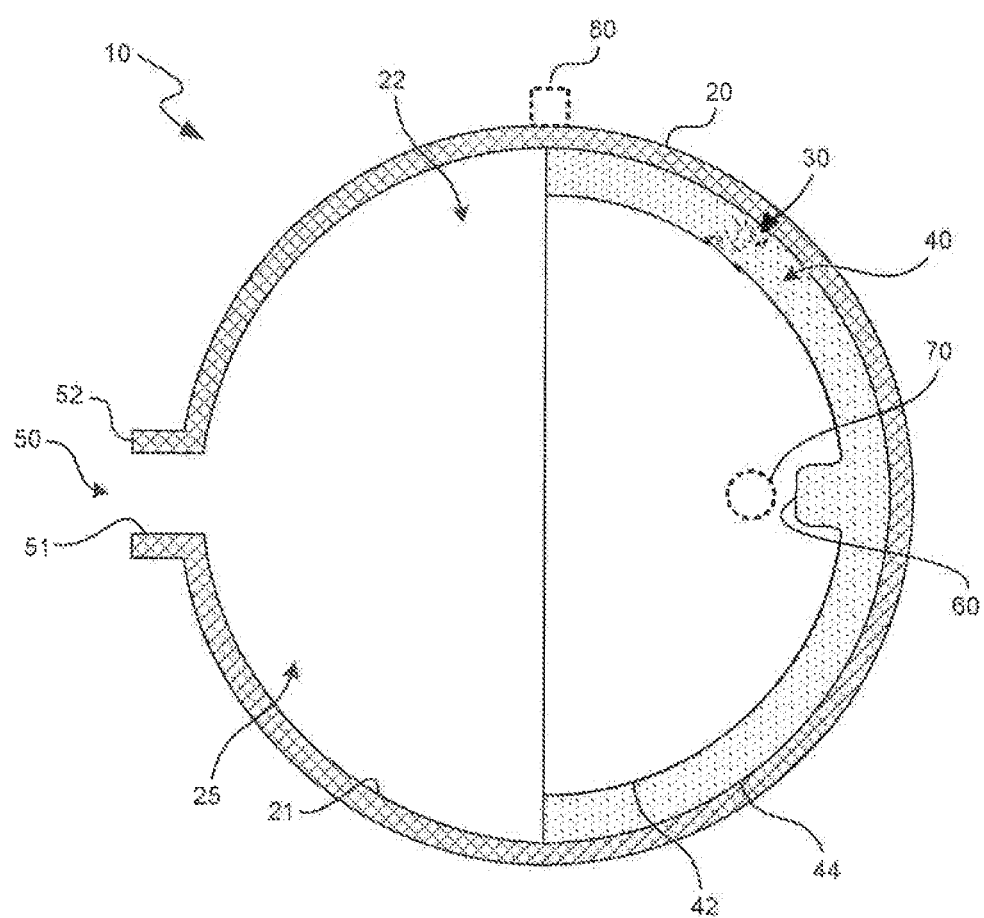
FIG. 7 is a cross-sectional view of the blood pump device of FIG. 5 in the second state in accordance with embodiments of the present technology.
Figure 8:
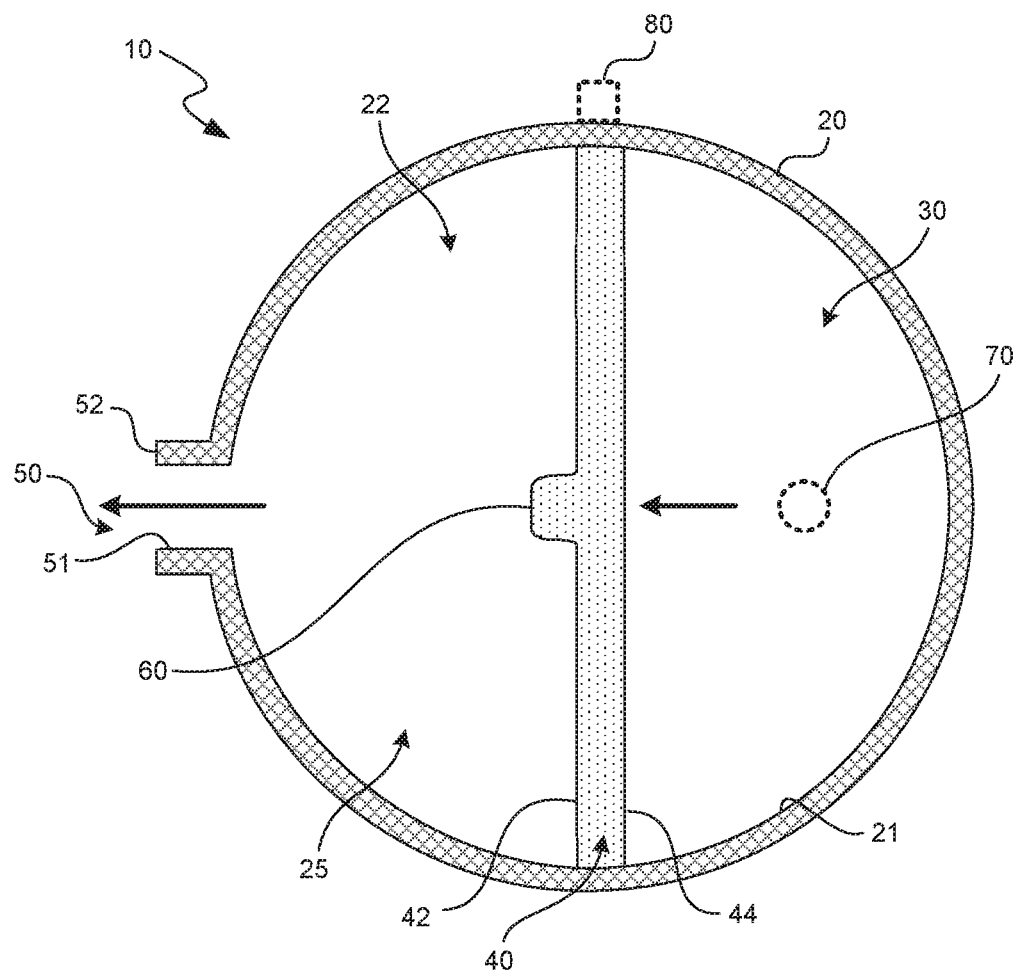
FIG. 8 is a cross-sectional view of the blood pump device of FIG. 5 transitioning between the second state and the first state in accordance with embodiments of the present technology.

Several features of the blood pump device 10 will now be discussed in detail with respect to FIGS. 5-8. FIGS. 5-8 are cross-sectional views of the blood pump device 10 taken on the cut-plane A-A of FIG. 1 and illustrate various stages of operation of the blood pump device 10. FIG. 5 illustrates the blood pump device 10 in a first configuration or state, FIG. 7 illustrates the blood pump device 10 in a second configuration or state, and FIGS. 6 and 8 illustrate the blood pump device 10 as it transitions between the first and second configurations.

Referring to FIGS. 5-8 together, the blood pump device 10 includes the housing 20 having an interior surface 21 that defines the internal reservoir 22, the flexible member 40 (e.g., a membrane or diaphragm) disposed within the internal reservoir 22, and the fluid outlet portion 50 that allows fluid to move into and out of the internal reservoir 22. The housing 20 can be constructed from rigid or semi-rigid materials such that the internal reservoir 22 has a fixed internal volume. The flexible member 40 can be attached to the interior surface 21 to divide the reservoir 22 into a first chamber 25 and a second chamber 30 that are fluidly isolated from each other. The flexible member 40 can extend over approximately half of the interior surface 21 of the housing 20. Thus, depending on the shape of the interior surface 21 of the housing 20, the flexible member 40 can have a hemispherical, half-cylindrical, or other shape that generally conforms over the interior housing surface 21. Accordingly, the flexible member 40 has a first surface 42 facing and defining a portion of the first chamber 25 and a second surface 44 facing and defining a portion of the second chamber 30. The fluid outlet portion 50 is fluidly coupled to the first chamber 25 such that fluid (e.g., blood) can flow into and out of the first chamber 25. The end section 52 of the fluid outlet portion 50 can be configured to directly connect to and project through a blood vessel wall (e.g., the subclavian artery) to place the blood vessel in communication with the first chamber 25. In some embodiments, for example, the end section 52 of the outlet portion 50 extends less than 20 mm, 15 mm, 10 mm or 5 mm into the blood vessel. In these and other embodiments, the outlet portion 50 can be configured to mate with the interface structure 90 (FIG. 4) to provide fluid communication between the blood vessel and the first chamber 25.

The flexible member 40 can be made from a flexible material that bends and flexes in response to fluid entering and exiting the internal reservoir 22 via the outlet portion 50. The flexible membrane 40 can be made from a variety of biocompatible materials that are resiliently flexible and capable of undergoing repeated cycles of deformation. For example, the flexible member 40 can be made from block copolymers, such as segmented polyether polyurethane. In some embodiments, the flexible membrane 40 is reinforced to provide durability and/or shape memory characteristics. For example, the flexible member 40 can be reinforced with a shape memory polymer, metal, or alloy, such as a medical grade steel or alloy (e.g., Nitinol®) that can be arranged in the form of a wire mesh. Additional or alternative stiffening elements and configurations known in the art can be incorporated into the flexible member 40. For example, polymer fibers, textiles and the like can be utilized. Additionally, the stiffening elements can be incorporated into the flexible member 40 in a variety of geometries, for example, as a mesh, braided or woven textile and the like.

As shown in FIG. 5, the flexible member 40 can include a plug element sized and shaped to fill the opening 51 of the outlet portion 50 when the blood pump device 10 is in the first configuration. While plug element 60 is depicted in FIGS. 5-8 as having a nipple or spheroid shape, any number of geometric shapes can be utilized to close off the opening 51 of the outlet portion 50 and prevent blood flow into the first chamber 25.

In operation, the blood pump device 10 transitions between the first configuration (FIG. 5) and the second configuration (FIG. 7) via movement of the flexible member 40 in response to fluid movement into and out of the outlet portion 50. As shown in FIG. 5, in the first configuration the flexible membrane 40 is positioned against or abuts the portion of the interior surface 21 of the housing 20 spaced proximate to the outlet portion 50. Thus, the first chamber 25 has a volume of zero or about zero, whereas the second chamber 30 can have a volume substantially equal to the fixed volume of the internal reservoir 22 (e.g., the volume of the internal reservoir 22 minus the volume of the flexible membrane). As shown in FIG. 7, in the second configuration the flexible membrane 40 is positioned apart from the portion of the interior housing surface 21 proximal to the outlet portion 50, causing the second chamber 30 to take on a second volume less than the fixed volume of the internal reservoir and the first chamber 25 to increase in volume. In the illustrated embodiment, the flexible membrane 40 abuts the portion of the interior housing surface 21 spaced away from or distal to the outlet portion 50 when the pump device 10 is in the second configuration. In some embodiments, when the pump device 10 is in the second configuration the second chamber 30 has a volume of less than 50%, less than 40%, less than 33%, less than 25%, less than 10%, and/or less than 5% of the volume of the internal reservoir 22. Accordingly, the first chamber 25 can have a first volume in the first configuration (e.g., 0) and a second volume in the second configuration that is greater than the first volume. Likewise, the second chamber 30 can have a first volume in the first configuration and a second volume in the second configuration that is less than the first volume.

FIG. 6 illustrates the blood pump device 10 in a first transition state moving in the direction of the arrow between the first configuration and the second configuration, FIG. 8 illustrates the blood pump device 10 in a second transition state moving in the direction of the arrow between the second configuration and the first configuration. During the first transition state, the movement of the flexible member 40 can generate negative pressure in the first chamber 25, thereby drawing fluid (e.g., blood from the blood vessel) into the first chamber 25 through the outlet portion 50 (as shown by the arrow). During the second transition state, movement of the flexible member 40 toward the outlet portion 50 can generate positive pressure in the first chamber 25, thereby pushing fluid (e.g., all or a portion of the fluid in the first chamber) out of the first chamber 25 through the outlet portion 50 (as shown by the arrow).

The housing 20 can be composed of a biocompatible material or combination of materials. In some embodiments, the housing 20 is constructed from materials that are sufficiently rigid (e.g., rigid or semi-rigid) to maintain the shape of the internal reservoir 22 under forces generated by transitioning of the blood pump device 10 between the first and second configurations. Many such materials are known in the art and envisioned for use in the blood pump device 10, such as, for example, medical grade metals and alloys including steel and titanium, as well as rigid polymers such as polycarbonates.

The blood pump device 10 can be configured to work in a pulsatile fashion such that movement of the flexible member 40 between the first and second configurations is synchronized with a patient's heartbeat. This movement of the flexible member 40 between the first and second configurations can be controlled by an actuator mechanism 12 (FIGS. 3A-3D). For example, the actuator mechanism 12 can transition between a first state (e.g., passive) and a second state (e.g., active). In some embodiments, when the actuator mechanism 12 is in the first state, the blood pump device 10 is in the first configuration with no fluid within the first chamber 25. When the actuator mechanism 12 switches to the second state, the flexible membrane 40 moves within the internal reservoir 22 to place the blood pump device 10 in the second configuration. As the flexible member 40 moves away from the outlet portion 50, the pump device 10 draws fluid through the outlet portion 50 into the first chamber 25 from the blood vessel 1 (FIGS. 1-4). When the actuator mechanism 12 is again transitioned to the first state (e.g., deactivated), the blood pump device 10 can automatically transition back to the first configuration in which the flexible member 40 moves towards the outlet portion 50. This generates a positive pressure in the first chamber 25 that causes fluid therein to expel from the first chamber 25, through the outlet portion 50, and into the blood vessel 1 coupled thereto. The blood pump device 10 can remain in the first configuration until the actuator mechanism 12 is transitioned back to the second state.

The blood pump device 10 can be designed such that it can remain in a passive state (i.e., the first configuration) with no or substantially no fluid in the internal reservoir 22 for an indefinite amount of time. The blood pump device 10 can then be activated and the actuator mechanism 12 cycled between first and second states, thereby controlling transition between first and second configurations for any given amount of time in synchrony with a patient's heartbeat. When pumping is deactivated (e.g., when the actuator mechanism 12 is retained in the first state), the flexible member 40 retains its position closing off the opening 51 of the outlet portion 50, thereby closing the first chamber 25 to fluid flow, and can do so for as long as necessary. As such, the absence, or substantial absence, of volume of the first chamber 25 when the blood pump device 10 is in the first configuration inhibits or prevents blood stagnation within the first chamber 25 and associated blood clot formation.

In some embodiments, the blood pumping system 100 (FIGS. 3A-3D) can be placed in a steady state requiring no energy while the blood pump device 10 is in the first configuration and the actuator mechanism 12 is in the first state, thereby decreasing the overall power needed to operate the system 100. In some embodiments, this low-energy configuration can be achieved by using shape memory materials for the flexible membrane 40. For example, the flexible membrane 40 can be made from or include a resiliently deformable polymer, alloy, metal, and/or other material that provides shape memory characteristics. In the non-deformed natural state, the shape-memory flexible membrane 40 can be sized and shaped in the configuration of the flexible membrane 40 in the first configuration. Transitioning the actuator mechanism 12 from a first state to a second state causes the flexible membrane 40 to mechanically deform into a second, non-natural shape, thereby causing the blood pump device 10 to transition to the second configuration. Once the actuator mechanism 12 is deactivated or transitioned back to the first state, the flexible membrane 40 automatically returns to its natural state and the blood pump device 10 returns to the first configuration.

In some embodiments, the blood pump device can use magnetism to control movement of the flexible member 40. For example, the flexible membrane 40 and/or the housing 20 can include one or more reversibly magnetic elements. The actuator mechanism 12 can selectively control magnetizing or demagnetizing the reversibly magnetic elements to initiate movement of the flexible member 40 and move the blood pump device 10 between the first and second configurations. In some embodiments, the flexible membrane 40 remains in the first state (e.g., wherein the volume of the first chamber is substantially zero) until a magnet is activated to pull the flexible membrane 40 to the second state.

In some embodiments, the blood pump system can include a pressurizable or pressurized fluid source that is in fluid communication with the second chamber 30 of the blood plump device 10. In such embodiments, the actuator mechanism 12 can mechanically control one or more valves 70 (shown in broken lines in FIGS. 5-8) to selectively pressurize or depressurize the second chamber 30. For example, the actuator mechanism 12 can open and close the valve 70. In the open position, fluid can enter the second chamber 30, thereby transitioning the blood pump device 10 from the second configuration to the first configuration. The actuator mechanism 12 can then create a pressure differential between the fluid source and the second chamber 30 to withdraw the fluid from the second chamber 30, thereby transitioning the blood pump device 10 from the first configuration to the second configuration. The valve 70 can then be closed to prevent fluid backflow. The fluid can be a liquid (e.g., saline solution) or a gas (e.g., air). In gas-based embodiments, the actuator mechanism 12 can open and close the valve 70 to selectively pressurize and depressurize the second chamber 30, thereby transitioning the blood pump device 10 between the first and second configurations. In some embodiments, a bellows or other fluid pressure system is connected to the blood pump device 10 to drive fluid into and out from the second chamber 30. Example bellows include those described in U.S. Pat. No. 8,066,628, filed Oct. 22, 2010 and entitled INTRA-AORTIC BALLOON PUMP AND DRIVER, and in U.S. Pat. No. 7,892,162, filed Oct. 22, 2009 and entitled ARTERIAL INTERFACE, the entire disclosures of which are each hereby incorporated by reference herein.

While the above embodiments are illustrative, one in the art will appreciate that functioning of the blood pump device 10 can be achieved in a variety of ways and the present technology therefore is not limited to a single embodiment.

Methods of Using the Present Technology

The blood pump device 10 of the present technology can be utilized to assist blood flow in a patient. As such, the present technology further provides methods for assisting blood circulation in a patient utilizing the blood pump device 10 in accordance with the present technology. The methods can include coupling the outlet portion 50 of the blood pump device 10 to a blood vessel 1 of a patient; drawing blood from the blood vessel 1 into the first chamber 25 by transitioning the flexible member 40 from a first position (when the blood pump device 10 is in the first configuration) to a second position (placing the blood pump device 10 in the second configuration); and expelling blood from the first chamber 25 though the outlet portion 50 into the blood vessel 1 by transitioning the flexible member 40 from the second position to the first position. In some embodiments, the actuator mechanism 12 can be used to transition the flexible member 40 between the first and second positions. For example, the actuator mechanism 12 can have a first state that transitions the flexible membrane 40 from the first position to the second position, and a second state that transitions the flexible membrane 40 from the second position to the first position.

In some embodiments, the blood pump device 10 can be directly coupled to a patient's vessel. In some embodiments, the outlet portion 50 is configured to directly couple to the vessel such that an external surface of the housing 20 is flush with an exterior facing wall of the blood vessel. This can prevent or inhibit accumulation of blood when the blood pump device 10 is in the passive state by reducing or minimizing the distance between the outlet portion 50 and the first chamber 25. As discussed above with respect to FIG. 4, in some embodiments the outlet portion 50 can include a flange or ring (e.g., a suture cuff) to facilitate suturing or other connection of the outlet portion 50 to the vessel wall. Alternatively or additionally, a flange or ring (e.g., a suture cuff, such as the interface member 90 of FIG. 4) can be attached to the wall of the vessel and then the outlet portion 50 can be coupled thereto. In embodiments where the external surface of the housing is not flush with the wall of the vessel, the blood pump device 10 can be configured to inhibit accumulation of blood within the outlet 50 or any conduit coupled between the outlet 50 and the vessel wall (e.g., via use of a plug element 60 or other structure).

In embodiments, activation of the blood pump device 10 is timed with the patient's heartbeat such that blood is drawn into the first chamber 25 during systole and expelled from the first chamber 25 during diastole. The blood pump device 10 can include one or more sensors 80 (shown schematically in FIGS. 5-8) to monitor the cardiac cycle. The actuator mechanism 12 can be operatively coupled to the one or more sensors 80 and one or more controllers having functionality for timing actuation of the blood pump device 10. In such embodiments, the sensors 80 can monitor the heartbeat and facilitate the actuator mechanism 12 to time its input to systole and diastole.

The volume of blood drawn into and subsequently ejected from the first chamber 25 during cycling of the blood pump device 10 is determined by the volume of the first chamber 25 when the device is in the second configuration. The internal reservoir 22 can be dimensioned such that the first chamber 25 draws and ejects a volume of fluid between about 40 to 60 cc, or about 40, 41, 42, 43, 44, 45, 46, 47, 48, 49, 50, 51, 52, 53, 54, 55, 56, 57, 58, 59 or 60 cc. In embodiments, the volume of the first chamber 25 in the second configuration can be varied or adjusted from cycle to cycle based on the cardiac rhythm by controlling the actuation mechanism 12.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

What is claimed is:

1. A system for pumping blood, the system comprising:
a blood pump device including:
a housing defining an internal reservoir having a volume;
a flexible member disposed within the internal reservoir defining a first chamber and a second chamber;
an outlet portion fluidly coupled to the first chamber, wherein the blood pump device is configured to transition between a first configuration and a second configuration via movement of the flexible member, the first chamber has a first volume that is substantially null in the first configuration, and the first chamber has a second volume greater than the first volume in the second configuration; and
an interface structure having an extension portion and a flange, wherein the extension portion is shaped to receive an end section of the outlet portion, the flange is configured to be anchored to an interior surface of a wall of a blood vessel of the patient's body, the flange is configured to cooperate with an outer surface of the interface structure to anchor a portion of the wall of the blood vessel between the flange and the housing, the outer surface of the interface structure is a second flange, and the second flange is configured to be positioned against an external surface of the vessel wall such that the first flange and the second flange substantially oppose one another.

2. The system of claim 1, further comprising an actuator mechanism configured to communicate with the blood pump device by a wired connection or wirelessly, the actuator mechanism being further configured to transform the blood pump device from the first configuration to the second configuration by causing the flexible member to at least partially move.

3. The system of claim 1, further comprising a skin interface device configured to facilitate access to the housing and/or flexible membrane from outside of the patient's body, wherein the actuator mechanism is configured to connect to the housing and/or to the flexible membrane via the skin interface device.

4. The system of claim 1, wherein the flexible membrane and the housing have one or more reversibly magnetic elements, and wherein the actuator mechanism controls the magnetization of the reversibly magnetic elements to transform the blood pump device between the first and second configurations.

5. The system of claim 1, wherein the second chamber includes a valve having an open position and a closed position, and wherein when in the open position, the second chamber is fluidly connected to a fluid source.

6. The system of claim 5, wherein the fluid connection between the second chamber and the fluid source allows fluid to enter the second chamber from the fluid source to transform the blood pump device from the second configuration to the first configuration.

7. The system of claim 1, wherein the flexible member comprises a shape memory material.

8. The system of claim 7, wherein the flexible member is in a first natural position in the first configuration and a second non-natural position in the second configuration.

9. The system of claim 8, wherein the actuator mechanism is configured to transform the flexible member into the second non-natural position when the actuator mechanism is activated.

10. The system of claim 1, wherein the actuator mechanism has a first state and a second state, and wherein when the actuator mechanism is in the first state, the blood pump device is in the first configuration, and wherein when the actuator mechanism is in the second state, the blood pump device is in the second configuration.

11. The system of claim 10, wherein the first state is a passive state and the second state is an active state.

12. The system of claim 11, wherein the blood pump device is configured to activate the actuator mechanism to the active state during the systole portion of the patient's cardiac cycle, thereby transitioning the blood pump device from the first configuration to the second configuration to draw fluid into the first chamber through the outlet portion.

13. The system of claim 11, wherein the blood pump device is configured to deactivate the actuator mechanism to the passive state during the diastole portion of the patient's cardiac cycle thereby transitioning the blood pump device from the second configuration to the first configuration to expel fluid out of the first chamber through the outlet portion.

14. The system of claim 13, wherein the flange is configured to cooperate with an outer surface of the housing of the blood pump device to anchor a portion of the blood vessel wall between the flange and the housing.

15. The system of claim 1, wherein the first flange and the second flange include a plurality of holes configured to facilitate suturing one or more of the first flange and the second flange to the blood vessel wall.

16. The system of claim 15, wherein the extension portion is a tubular structure with a first end and a second end, the first end of the tubular structure is shaped to receive the end section of the outlet portion, and one or more of the first flange and the second flange radially extends from the second end of the tubular structure.

* * * * *